(12) United States Patent
Haam et al.

(10) Patent No.: US 10,136,662 B2
(45) Date of Patent: Nov. 27, 2018

(54) ORAL VIRUS VACCINE

(71) Applicant: University-Industry Foundation, Yonsei University, Seoul (KR)

(72) Inventors: Seungjoo Haam, Seoul (KR); Hyun-Ouk Kim, Seoul (KR); Jong Woo Lim, Seoul (KR)

(73) Assignee: University-Industry Foundation, Yonsei University, Seoul (KR)

( * ) Notice: Subject to any disclaimer, the term of this patent is extended or adjusted under 35 U.S.C. 154(b) by 21 days.

(21) Appl. No.: 15/211,091

(22) Filed: Jul. 15, 2016

(65) Prior Publication Data

US 2017/0014350 A1 Jan. 19, 2017

(30) Foreign Application Priority Data

Jul. 16, 2015 (KR) ........................ 10-2015-0100878

(51) Int. Cl.

| | |
|---|---|
| *A61K 39/125* | (2006.01) |
| *A61K 9/50* | (2006.01) |
| *A61K 39/00* | (2006.01) |
| *A23K 50/30* | (2016.01) |
| *A23K 10/18* | (2016.01) |
| *A61K 39/225* | (2006.01) |
| *A23K 40/30* | (2016.01) |
| *A23K 10/16* | (2016.01) |
| *A23K 50/40* | (2016.01) |
| *A61K 39/12* | (2006.01) |

(52) U.S. Cl.
CPC .............. *A23K 10/18* (2016.05); *A23K 10/16* (2016.05); *A23K 40/30* (2016.05); *A23K 50/30* (2016.05); *A23K 50/40* (2016.05); *A61K 9/5026* (2013.01); *A61K 39/12* (2013.01); *A61K 39/225* (2013.01); *A61K 2039/542* (2013.01); *A61K 2039/552* (2013.01); *C12N 2770/20023* (2013.01); *C12N 2770/20034* (2013.01)

(58) Field of Classification Search
None
See application file for complete search history.

(56) References Cited

U.S. PATENT DOCUMENTS 3,725,545 A * 4/1973 Maes .................... A61K 39/39
424/216.1
3,823,228 A * 7/1974 Ferris .................. A61K 9/1676
424/223.1
4,152,413 A * 5/1979 Goodnow .......... A61K 39/0225
424/262.1

FOREIGN PATENT DOCUMENTS

| GB | 1290141 A | * 9/1972 | ............. A61K 39/39 |
|---|---|---|---|
| KR | 1998-0011874 | 4/1998 | |
| KR | 20040092760 A | * 11/2004 | |

OTHER PUBLICATIONS

Rowe, Raymond C., Paul J. Sheskey, and Marian E. Quinn, eds. Handbook of pharmaceutical excipients. vol. 6. London: Pharmaceutical press, 2006, pp. 525-533.*
Particle Size Conversion Table. Sigma Aldrich (Dec. 2012).*
Song, Daesub, and Bongkyun Park. "Porcine epidemic diarrhoea virus: a comprehensive review of molecular epidemiology, diagnosis, and vaccines." Virus genes 44.2 (2012): 167-175.*
Davitt, Christopher JH, and Ed C. Lavelle. "Delivery strategies to enhance oral vaccination against enteric infections." Advanced drug delivery reviews 91 (2015): 52-69.*
Lavelle, Ed C., and D. T. O'Hagan. "Delivery systems and adjuvants for oral vaccines." Expert opinion on drug delivery 3.6 (2006): 747-762.*
Delgado, A., et al. "PLG microparticles stabilised using enteric coating polymers as oral vaccine delivery systems." Vaccine 17.22 (1999): 2927-2938.*
Notification of Reason for Refusal dated Oct. 14, 2016 From the Korean Intellectual Property Office Re. Application No. 10-2015-0100878 and Its Summary in English. (9 Pages).
Bolhassani et al. "Polymeric Nanoparticles. Potent Vectors for Vaccine Delivery Targeting Cancer and Infectious Diseases", Human Vaccines & Immunotherapeutics, 10(2): 321-332, Published Online Oct. 15, 2013.
Yoshida et al. "pH- and Ion-Sensitive Polymers for Drug Delivery", Expert Opinion on Drug Delivery, 10(11): 1497-1513, Nov. 2013.

* cited by examiner

*Primary Examiner* — David J Blanchard
*Assistant Examiner* — Peter Anthopolos

(57) ABSTRACT

The present disclosure relates to a polymer-coated virus particle for an oral virus vaccine, a method of preparing the same, and a composition comprising the same. In accordance with the present disclosure, the oral virus vaccine can be effectively delivered to the intestines without being destroyed even in the low pH environment of the gastrointestinal tract, then the prevention efficacy against viral infections can be improved.

9 Claims, 2 Drawing Sheets
(2 of 2 Drawing Sheet(s) Filed in Color)

FIG. 1

Porcine epidemic
diarrhea virus vaccine
(PEDV vaccine)

Polycationic
Amino Acid

PEDV vaccine
coated with
Polycationic
Amino Acid pH sensitive
Amino acid

PEDV vaccine
coated with
pH sensitive
Polymer

ORAL VIRUS VACCINE

RELATED APPLICATION

This application claims the benefit of priority of Korean Patent Application No. 10-2015-0100878 filed on Jul. 16, 2015, the contents of which are incorporated herein by reference in their entirety.

FIELD AND BACKGROUND OF THE INVENTION

The present invention relates to an oral virus vaccine and a method of preparing the same.

Viral infectious diseases refer to diseases occurring in hosts infected with viruses. Viruses cause various symptoms depending upon infected sites and infection types. The most common symptoms caused by enteric infection are diarrhea, peritonitis, etc.

As a representative example, porcine epidemic diarrhea (PED) was first reported in Belgium and Britain in 1978 and, thereafter, occurred in many countries (Asia including Japan, China, and South Korea and throughout Europe) in which pigs are raised. In particular, it causes great economic loss in Europe and Asia. The porcine epidemic diarrhea virus (PEDV) causing porcine epidemic diarrhea mainly proliferates in small intestine villous cells and degenerates or necrotizes villus epithelial cells. Accordingly, shrinkage and detachment of villi occur and malabsorption is caused, whereby continuous watery diarrhea occurs. Porcine enteritis occurs regardless of age, and is accompanied by severe diarrhea and dehydration. Further, the mortality rate among piglets can reach 80 to 90%.

In the Republic of Korea, porcine epidemic diarrhea greatly prevailed for two years after the PED virus was first introduced in 1992. At this moment, the PED virus is not clinically distinguishable from transmissible gastroenteritis virus (TGEV), resulting in significant economic damage. Recently, co-infection with the PED virus along with the TGE virus is increasing relative to infection with the PED virus only. Such infection occurs in all seasons, but most frequently occurs in winter. Prevention of the porcine epidemic diarrhea having a high onset rate and mortality rate is of utmost importance. At present, an oral PEDV vaccine for neutralizing external viruses in the intestine is commercially available.

Oral virus vaccines are advantageous in that pain and stress are not encountered upon administration and, accordingly, easy administration is possible. In addition, oral virus vaccines have advantages such as convenient supply and distribution. Oral virus vaccines need to be stably delivered to the intestines, but become unstable in the gastrointestinal tract having a low pH environment due to gastric acid. Accordingly, the effects of vaccines are reduced.

Therefore, there is a need for technology for delivering effectively oral virus vaccines to the intestines, without destruction of the virus vaccines even in a low pH environment.

RELATED ART DOCUMENT

Patent Document (Patent Document 1) Korean Patent Laid-Open Publication No. 1998-0011874

SUMMARY OF THE INVENTION

Therefore, the present invention has been made in view of the above problems, and it is an object of the present invention to provide a polymer-coated virus particle for an oral vaccine to stably protect and deliver the oral virus vaccine in a low pH environment, without destruction of the virus vaccine, a method of preparing the same, a vaccine composition comprising the same, a feed composition comprising the same and a method of presenting viral infection administrating the same.

In accordance with the present invention, the above and other objects can be accomplished by the provision of a polymer-coated virus particle for an oral vaccine, comprising: one or more virus particles for use as an oral vaccine; a cationic polymer layer; and a pH-sensitive polymer layer, wherein the cationic polymer layer and the pH-sensitive polymer layer are formed to surround one or more virus particles, and any one of the cationic polymer layer and the pH-sensitive polymer layer is formed as an inner layer, and the other is formed as an outer layer. In accordance with another aspect of the present invention, there is provided a method of preparing a polymer-coated virus particle, the method comprising: a step of formation of an inner layer to surround virus particles by mixing virus particles for use as an oral vaccine with cationic polymers or pH-sensitive polymers; and a step of formation of an outer layer to surround the inner layer by mixing the virus particles, which are surrounded by the inner layer, with cationic polymers or pH-sensitive polymers, wherein any one of cationic polymers and pH-sensitive polymers forms the inner layer, and the other forms the outer layer.

In accordance with yet another aspect of the present invention there is provided an oral vaccine composition comprising one or more polymer-coated virus particles according to the present invention.

In accordance with yet another aspect of the present invention there is provided a feed composition comprising one or more polymer-coated virus particles according to the present invention.

In accordance with yet another aspect of the present invention there is provided a method of preventing viral infection, the method comprising orally administrating an effective amount of the polymer-coated virus particles to a subject.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing in detail exemplary embodiments thereof with reference to the accompanying drawings, in which:

FIG. 1 is a schematic diagram illustrating the structure of a polymer-coated virus particle for an oral virus vaccine according to an embodiment of the present disclosure;

DESCRIPTION OF SPECIFIC EMBODIMENTS OF THE INVENTION

Figures 2, 3:
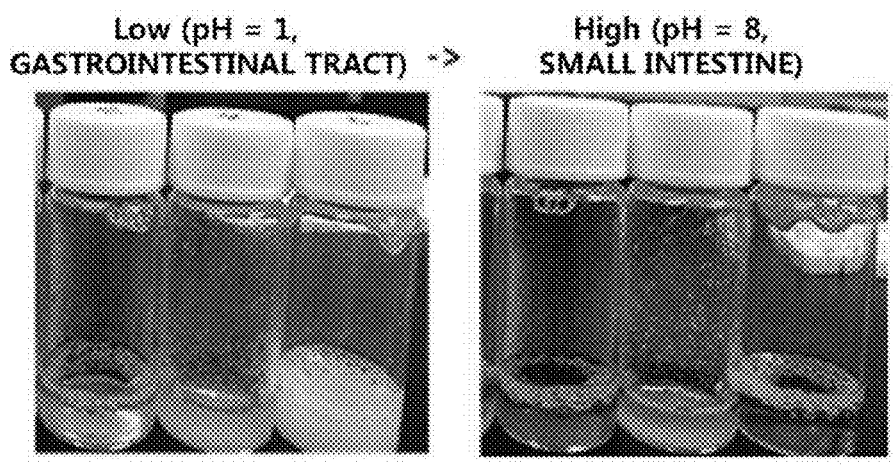
FIG. 2 illustrates pH change in a polymer-coated virus particle for an oral virus vaccine according to an embodiment of the present disclosure.
FIG. 3 illustrates stability change in a polymer-coated virus particle for an oral virus vaccine according to an embodiment of the present disclosure dependent upon pH change.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Oral virus vaccines for preventing infection by viruses proliferating in the intestines should pass through the gastrointestinal tract to reach intestines. Unlike the intestines, the gastrointestinal tract has a low pH of 1 to 3. Accordingly, virus vaccines should have a property that be stably maintained even under a low pH condition. However, currently available oral virus vaccines are unstable at low pH, and thus, it is difficult to efficiently deliver vaccines to the intestines. Accordingly, virus prevention effects of vaccines are not efficient.

Therefore, the present inventors repeatedly conducted research to address problems in delivering oral virus vaccines. As a result, the present inventors confirmed that, by using a cationic polymer and a pH-sensitive polymer, oral virus vaccine can be stably delivered to the intestines without destruction of virus particles for use as vaccine, even under a low pH condition, thus completing the present disclosure.

Therefore, the present disclosure provides a polymer-coated virus particle for an oral virus vaccine comprising one or more virus particles for use as an oral vaccine which are surrounded by a cationic polymer layer and a pH-sensitive polymer layer. FIG. 1 illustrates the configuration of a polymer-coated virus particle for an oral virus vaccine according to an embodiment of the present disclosure and a method of preparing the same as a schematic diagram. In the present disclosure, the cationic polymer layer and the pH-sensitive polymer layer may be formed to surround one or more virus particles in any order, and any one of the layers is formed as an inner layer, and the other is formed as an outer layer.

In the present disclosure, the expression "forming a layer or formation of layer" refers to the case in which another component is further included between corresponding components, as well as the case in which the corresponding components are stacked while directly contacting each other. For example, the case in which a second component is formed on a surface of a first component while directly contacting the surface, as well as the case in which a third component is further formed between the first and second components are included.

In the present disclosure, the expression "being formed to surround on component" means to form a layer on the surface of the component which is included inside the layer. The expression also refers to encapsulation or coating. According to an embodiment of the present disclosure, the polymer layers may be formed on the surface of one or more virus particles or the polymer layer may be encapsulate one or more virus particles.

The virus particles which are contained inside the polymer layer may be a single particle or may be a plurality of particles such as a cluster.

According to an embodiment of the present disclosure, provided is a polymer-coated virus particle comprising one or more virus particles for use as an oral vaccine; a cationic polymer layer; and a pH-sensitive polymer, wherein the cationic polymer layer forms inner layer to surround one or more virus particles and the pH-sensitive polymer layer forms outer layer to surround inner layer.

According to another embodiment of the present disclosure, provided is a polymer-coated virus particle comprising one or more virus particles for use as an oral vaccine; a cationic polymer layer; and a pH-sensitive polymer, wherein pH-sensitive polymer layer forms inner layer to surround one or more virus particles and the cationic polymer layer forms outer layer to surround inner layer.

The virus particles refer to effective ingredients that are artificially introduced into the human body before infection by a pathogen and trigger an immune response. For example, the virus particles may be, without being limited to, attenuated or inactivated pathogens, proteins, or fragments. The virus particles are preferably present as solids, but may be present as aqueous solutions, depending upon the vaccine types.

In an embodiment, an average particle diameter of the virus particles may be, without being limited to, 0.1 to 10 µm. However, the virus particles need not have a completely globular shape. Examples of the shapes of the virus particles include a globular-like shape, an ovoid shape wherein the diameter of a portion is longer than other portions, a quadrangular-like shape, etc.

The virus particles may exhibit a charge on surfaces thereof. Examples of the charge include all of a neutral charge, a negative charge, and a positive charge. The polymer layers formed on the particles may be included in the polymer-coated virus particles in any order, regardless of the charge of the particles. In one preferred embodiment, when the polymer-coated virus particles have a negative charge, the polymer-coated virus particles of the present disclosure may include a cationic polymer layer formed to surround one or more particles and a pH-sensitive polymer layer formed to surround the cationic polymer layer. In addition, when the virus particles have a positive charge, the polymer-coated virus particles of the present disclosure may include a pH-sensitive polymer formed to surround one or more particles and a cationic polymer layer formed to surround the pH-sensitive polymer layer. In addition, when the virus particles hardly exhibit a charge or exhibit a neutral charge, the polymer-coated virus particles may include a pH polymer layer and a cationic polymer layer, the order of which is not limited, formed on each of the particles. However, these are provided as examples to easily form polymer layers, and the present invention is not limited thereto.

In the present disclosure, the virus particles are not limited so long as they are a vaccine against viruses causing enteric infection. For example, the oral virus vaccine according to an embodiment of the present disclosure may be a vaccine against a virus included in any one genus of alpha corona virus, rotavirus, sapovirus, feline enteric corona virus, parvovirus, and calicivirus. More particularly, the oral virus vaccine may be a virus vaccine for preventing infection by a virus selected from the group consisting of epidemic diarrhea virus, transmissible gastroenteritis (TGE) virus, rotavirus, enteric calicivirus, panleukopenia virus, infectious peritonitis virus, parvovirus, and norovirus.

A subject to be administered the virus particles may be a mammal including humans. Specific examples of the subject include pigs, cats, dogs, and humans.

More particularly, the vaccine may be a virus vaccine for preventing viral infectious diseases due to a virus selected from the group consisting of porcine epidemic diarrhea (PED) virus, porcine transmissible gastroenteritis (TGE) virus, rotavirus, porcine enteric calicivirus, feline panleukopenia virus, feline infectious peritonitis (FIP) virus, canine parvovirus, and norovirus.

The oral vaccine against porcine epidemic diarrhea virus (PEDV) according to an embodiment of the present disclosure may be used without specific limitation so long as it is an oral vaccine for preventing and treating infection by PEDV. For example, the oral vaccine against PEDV is available from Green Cross Veterinary Products Co., Ltd. The commercially available oral vaccine against PEDV has highest stability at pH 7 to 8. At pH 5 or less, or pH 11 or more, the virus particles for use as a vaccine are rapidly extinguished and destroyed. Accordingly, in this case, it is difficult to efficiently deliver the virus particles for use as a vaccine to the intestines. However, when the virus particles for oral vaccine against PEDV are coated with the pH-sensitive polymer layer and a cationic polymer layer, the virus particles are advantageously not extinguished or destroyed even at a low pH such as pH 5 or less, or pH 1 to 3 (see examples below).

Since the virus particles for oral vaccine against PEDV exhibits weak negative charge, a coating layer composed of a cationic polymer may be more satisfactorily formed on the surface of the virus particles. By forming the cationic polymer layer, the stability of the virus particles may be maintained even at low pH. In addition, since the cationic polymer layer is decomposed by a serine based protease, e.g., trypsin, etc. present within the intestines, the virus vaccine may be efficiently delivered into the intestines.

In an embodiment of the present disclosure, the cationic polymer may be particularly a cationic polyamino acid. Examples of the cationic polymer include, without being limited to, polylysine, polyhistidine, and polyarginine. The cationic polymer layer may include one or more cationic polymers or may be composed of one or more cationic polymers.

In an embodiment of the present disclosure, the cationic polymer may be represented by Formula 1 below:

$$(\text{poly-M})k, \quad [\text{Formula 1}]$$

wherein M is lysine, histidine, or arginine, and k is 2 to 50.

In an embodiment, the average thickness of the cationic polymer layer may be 1 nm to 1 μm, 5 nm to 500 nm, 10 nm to 300 nm, 10 nm to 200 nm, 10 nm to 100 nm, 10 nm to 90 nm, 10 nm to 70 nm, 10 nm to 50 nm, 10 nm to 30 nm, or 10 nm to 20 nm. The virus particles coated with the polymer layer that have these ranges of thickness are stably maintained even in the condition of pH 1-3, do not stimulate an immune reaction, and may be effectively delivered to target sites, i.e., the intestines without destruction of the virus particles. Therefore, the administration efficacy of vaccine for preventing viral infections can be improved. In addition, when the pH-sensitive polymer layer is formed on the cationic polymer layer and the thickness of the cationic polymer layer is within the ranges, the pH-sensitive polymer layer is satisfactorily formed.

In the present disclosure, the structure of the pH-sensitive polymer layer is maintained at pH 1 to 3, and the pH-sensitive polymer layer is ionized at pH 7 to 9. For example, the pH-sensitive polymer according to an embodiment of the present disclosure has a pKa of 4.66 and a pKb of 7.0. When the pH-sensitive polymer has a pKa of less than 4.66, hydrogen bonds in the polymer layer are maintained and thus the structure of the pH-sensitive polymer is stably maintained. When the pH-sensitive polymer has a pKa of greater than 7.0, the polymer is ionized and thus anions are formed. As a result, electrostatic repulsion is induced and thus the polymer is decomposed, thereby the virus particles are released. Accordingly, thanks to formation of the pH-sensitive polymer layer, it is able to prevent an extinguishment and/or destruction of the virus particles that appear in low pH ranges, to maintain the stability of the particles in the low pH ranges, and to release the virus particles under pH conditions of the interiors of intestines.

In an embodiment of the present disclosure, the pH-sensitive polymer layer is characterized by being ionized at pH 7 to 9.

In an embodiment, the pH-sensitive polymer layer may comprise, without being limited to, an acrylate-based polymer. Alternatively, the pH-sensitive polymer layer may be consisting of an acrylate-based polymer, but the present invention is not limited thereto.

The acrylate-based polymer may be, without being limited to, one or more selected from the group consisting of poly(methacrylic acid-co-ethyl acrylate), poly(methacrylic acid-co-methyl methacrylate), and poly(methyl acrylate-co-methyl methacrylate-co-methacrylic acid). As commercially available acrylate-based polymers, there are L 30 D-55, L 100-55, L 100, L12.5, S 100, S 12.5, and FS 30 D manufactured by EUDRAGIT®. The weight average molar mass of the acrylate-based polymer may be 100000 to 400000 g/mol, 100000 to 350000 g/mol, or 120000 to 330000 g/mol.

In an embodiment, the average thickness of the pH-sensitive polymer layer may be 1 nm to 1 μm, 5 nm to 500 nm, 10 nm to 300 nm, 10 nm to 200 nm, 10 nm to 100 nm, 10 nm to 90 nm, 10 nm to 70 nm, 10 nm to 50 nm, 10 nm to 30 nm, or 10 nm to 20 nm. The virus particles coated with the polymer layer that have these ranges of thickness are stably maintained even in the condition of pH 1-3, do not stimulate an immune reaction, and may be effectively delivered to target sites, i.e., the intestines without destruction of the virus particles. Therefore, the administration efficacy of vaccine for preventing viral infections can be improved. In addition, such an effect may be maximized when the thicknesses of the cationic polymer layer and the pH-sensitive polymer layer are respectively within the ranges.

In an aspect of the purpose of the present invention in order to deliver virus particles effectively to the intestines, the present disclosure also provides a vaccine delivery system. The vaccine delivery system comprises one or more virus particles for use as an oral vaccine; a cationic polymer layer; and a pH-sensitive polymer layer, wherein the cationic polymer layer and the pH-sensitive polymer layer are formed to surround one or more virus particles, and any one of the cationic polymer layer and the pH-sensitive polymer layer is formed as an inner layer, and the other is formed as an outer layer.

The present disclosure also provides a method of preparing the Polymer-coated virus particle for an oral virus vaccine, the method comprising a step of formation of an inner layer to surround virus particles by mixing virus particles for use as an oral vaccine with cationic polymers or pH-sensitive polymers; and a step of formation of an outer layer to surround the inner layer by mixing the virus particles, which are surrounded by the inner layer, with cationic polymers or pH-sensitive polymers, wherein any one of cationic polymers and pH-sensitive polymers forms the inner layer, and the other forms the outer layer. As described above, the cationic polymer layer and the pH-sensitive polymer layer may be stacked in any order.

In one embodiment, the method may comprise a step of mixing the oral virus particles with the cationic polymer to form a cationic polymer layer on the surface of one or more virus particles; and a step of mixing the virus particles which are surrounded by the cationic polymer layer as inner layer, with the pH-sensitive polymer to form a pH-sensitive polymer layer as outer layer on the cationic polymer layer.

In other embodiments, the method may comprise a step of mixing the virus particles with the pH-sensitive polymer to form a pH-sensitive polymer layer on the surface of one or more virus particles; and a step of mixing the virus particles which are surrounded by the pH-sensitive polymer layer as inner layer, with the cationic polymer to form a cationic polymer layer as outer layer on the pH-sensitive polymer layer.

In the present disclosure, the virus particles are not specifically limited so long as the vaccine is a vaccine against intestinal viruses. For example, the oral virus vaccine according to an embodiment of the present disclosure may be a vaccine against a virus included in any one genus of alpha corona virus, rotavirus, sapovirus, feline enteric corona virus, parvovirus, and calicivirus.

The virus particles and the viruses have been described above.

In an embodiment, an average particle diameter of the virus particles may be, without being limited to, 0.1 to 10 μm. However, the virus particles are not required to have a completely globular shape. Examples of the shapes of the oral virus particles include a globular-like shape, an ovoid shape wherein the diameter of a portion is longer than other portions, a quadrangular-like shape, etc.

In an embodiment, the pH-sensitive polymer layer may be formed in a pH range of 7 or less, or 5 to 6. Since the pH-sensitive polymer of the present disclosure is ionized at pH 7 to 9, the pH-sensitive polymer layer may be smoothly formed in the pH ranges without denaturalization or destruction of the virus particles. In addition, within the pH ranges, the cationic polymer layer may be formed and all preparation processes of the polymer-coated virus particles for an oral virus vaccine may be carried out.

In an embodiment, the pH-sensitive polymer layer may comprise, without being limited to, an acrylate-based polymer. Alternatively, the pH-sensitive polymer layer may be consisting of an acrylate-based polymer, but the present invention is not limited thereto.

The acrylate-based polymer may be, without being limited thereto, one or more selected from the group consisting of poly(methacrylic acid-co-ethyl acrylate), poly(methacrylic acid-co-methyl methacrylate), and poly(methyl acrylate-co-methyl methacrylate-co-methacrylic acid). As commercially available acrylate-based polymers, there are L 30 D-55, L 100-55, L 100, L 12.5, S 100, S 12.5, and FS 30 D manufactured by EUDRAGIT®. The weight average molar mass of the acrylate-based polymer may be 100000 to 400000 g/mol, 100000 to 350000 g/mol, or 120000 to 330000 g/mol.

In an embodiment, the pH-sensitive polymer may be included in an amount of 0.5 to 20 parts by weight, 1 to 15 parts by weight, or 5 to 10 parts by weight based on 100 parts by weight of the virus particles. Within these ranges, the pH-sensitive polymer layer may be formed with a suitable thickness for oral vaccines.

In an embodiment, the cationic polymer may be, without being limited to, one or more selected from the group consisting of polylysine, polyhistidine, and polyarginine.

In an embodiment, the cationic polymer may be represented by Formula 1 below:

$$(\text{poly-M})_k, \quad [\text{Formula 1}]$$

wherein M is lysine, histidine, or arginine, and k is 2 to 50.

In an embodiment, the cationic polymer may be mixed in an amount of 0.5 to 20 parts by weight, 1 to 15 parts by weight, or 5 to 10 parts by weight based on 100 parts by weight of the virus particles. Within these ranges, the cationic polymer layer may be formed with a suitable thickness for oral vaccines.

The present disclosure also provides an oral vaccine composition comprising one or more polymer-coated virus particles according to the present disclosure.

The oral vaccine composition may further comprise an additional component such as carrier, adjuvant etc. in addition to the viral particles of the present invention. Specific description thereof is the same as that given above.

The present disclosure also provides a feed composition comprising one or more polymer-coated virus particles according to the present disclosure.

The feed composition may further comprise an effective amount of one or more of dietary ingredients selected from the traditional group of minerals, including, but not limited to, magnesium, selenium, zinc, chromium, fatty acid and mixtures thereof. Specific description thereof is the same as that given above.

The present disclosure also provides a method of preventing viral infection, the method comprising orally administrating an effective amount of the polymer-coated virus particles according to the present disclosure to a subject.

In the present disclosure, the virus particles are not specifically limited so long as the vaccine is a vaccine against intestinal viruses. Specific description thereof is the same as that given above.

The oral administration may be performed by a common method of orally administrating a vaccine or a pharmaceutical agent. A particular administration frequency, administration amount, and administration method may be determined considering the age, weight, and sex of a subject and other characteristics thereof.

In one example, the administration may be administered in a form of the virus particle itself; or a mixture with other consistent such as compositions. The compositions may include food compositions, feed compositions, and vaccine compositions, etc.

The effective amount may be administrated once or divided into several doses.

The viral infection refers to a phenomenon wherein viruses invade into a subject and, accordingly, cells, etc. are infected. A virus particle type contained in the polymer layer may be dependent upon virus types causing infectious diseases. In particular, superior prevention effects may be obtained by increasing vaccine delivery efficiency and stability of the vaccine with respect to intestinal viruses.

Now, the present invention will be described in more detail with reference to the following examples. These examples are provided for illustrative purposes only and should not be construed as limiting the scope and spirit of the present invention.

EXAMPLE

Comparative Example 1

Preparation of Virus Particles Coated with Cationic Polymer Layer 30 mg of polylysine, as a cationic polymer, was dissolved in 1 ml of Dulbecco Modified Eagle Medium (DMEM). A small amount, i.e., 1 ml, of a resultant mixture was added dropwise to 5 ml of an aqueous oral virus vaccine solution (vaccine against porcine epidemic diarrhea virus (PEDV) manufactured by Green Cross Veterinary Products Co., Ltd.) at pH 5 to 6 while stirring at 600 rpm. Subsequently, stirring was further performed at 600 rpm for one hour. As a result, the virus particles contained the aqueous oral virus vaccine solution were coated with the cationic polymer.

Comparative Example 2

Preparation of Virus Particles Coated with pH-sensitive Polymer Layer 20 mg of a pH-sensitive polymer (Eudragit S100) was dissolved in a co-solvent composed of 1 ml of ethanol and 1 ml of DMEM. 50 µl of a resultant mixture was added dropwise to 5 ml of an aqueous oral virus vaccine (PEDV, Green Cross Veterinary Products Co., Ltd.) solution stirred at 600 rpm. A resultant mixture was stirred at 600 rpm to remove the ethanol solvent. As a result, the virus particles contained the aqueous oral virus vaccine solution were coated with the pH-sensitive polymer.

Preparation Example 1

Preparation of Virus Particles Coated with Cationic Polymer Layer-pH-sensitive Polymer Layer 20 mg of a pH-sensitive polymer (Eudragit S100) was dissolved in a co-solvent composed of 1 ml of ethanol and 1 ml of DMEM. With stirring at 600 rpm, 50 µl of the pH-sensitive polymer mixture was added dropwise to 5 ml of the solution of Comparative Example 1 that contains the virus particles coated with the cationic polymer. With further stirring at 600 rpm for one hour, the ethanol solvent was removed. As a result, virus particles coated with the cationic polymer layer (as an inner layer) and the pH-sensitive polymer layer (as an outer layer) was prepared. FIG. 1 illustrates a preparation process of the polymer-coated virus particles for an oral virus vaccine according to the present disclosure.

Preparation Example 2

Preparation of Virus Particles Coated with pH-sensitive Polymer Layer-cationic Polymer Layer 30 mg of polylysine, as a cationic polymer, was dissolved in 1 ml of DMEM. With stirring at 600 rpm, 1 ml of the cationic polymer mixture was added dropwise to 5 ml of the solution according to Comparative Example 2 that contains the virus particles coated with the pH-sensitive polymer. A resultant mixture was further stirred at 600 rpm for one hour, thereby preparing virus particles coated with the pH-sensitive polymer layer (as an inner layer) and the cationic polymer layer (as an outer layer).

Experimental Example 1

Investigation of Stability of Polymer-coated Virus Particles for an Oral Virus Vaccine Behavior change, i.e., stability of the polymer-coated virus particles for an oral virus vaccine according to the present disclosure dependent upon pH change was investigated using a Porcine Epidemic Diarrhea Virus Rapid Kit (PEDV Rapid Kit).

The virus particles for an oral porcine epidemic diarrhea virus (PEDV) vaccine at pH 7 to 8 without polymer layer, the virus particles for the oral PEDV vaccine at pH 5 to 6 without polymer layer, and the virus particles for the oral PEDV vaccine coated only with the pH-sensitive polymer (Comparative Example 2) were used as control groups. The polymer-coated virus particles of Preparation Example 1 (the cationic polymer layer was an inner layer) and the polymer-coated virus particles of Preparation Example 2 (the pH-sensitive polymer layer was an inner layer) were used as experimental groups. The stability of each of the virus particles for an oral virus vaccine of the three control groups and the two experimental groups was investigated using the PEDV rapid kit.

To investigate response change dependent upon pH, pH was lowered to pH 1 to 2, similar to the pH of the interior of the gastrointestinal tract, and then elevated to pH 7.6 to 8.5, similar to the pH of the interior of the intestines. The stability of each of the virus particles was investigated using the rapid kit.

Prior to the stability investigation, pH change was investigated with phenol red as a pH indicator. The virus particles of the each group were treated with DMEM including phenol red. The pH was lowered to pH 1, similar to the pH of the interior of the gastrointestinal tract, and then elevated to pH 8, similar to the pH of the interior of the intestines, followed by investigating color change. As a result, it can be confirmed, as illustrated in FIG. 2, that the environment of the virus particles of the each group was changed to the interior pH conditions of the gastrointestinal tract and the intestines through color change of phenol red (yellow at pH 6.8 or less, and red (purple) at pH 6.8 to 8).

Experimental results by means of the rapid kit were illustrated in FIG. 3. In FIG. 3, a control was a positive control, and thus, should exhibit a line upon the use of the rapid kit. The TEST line was provided to indicate the existence or absence of PEDV. The appearance of the TEST line indicated the existence of PEDV.

In FIG. 3, sample No. 1 referred to pure virus particles for oral PEDV vaccine (pH 8.77) without coating layer.

Sample No. 2 referred to pure virus particles for oral PEDV vaccine (pH 5.8) without coating layer. Sample No. 2 (low->high) indicated a result of Sample No. 2, the pH of which was lowered to pH 1 and then elevated to pH 8.

Sample No. 3 (primary) referred to virus particles for the PEDV vaccine of Sample No. 2 coated with a cationic polymer polylysine (pLys). Sample No. 3 (secondary) referred to virus particles of the Sample No. 3 (primary) additionally coated with the pH-sensitive polymer layer. And Sample No. 3 (low->high) indicated a result of Sample No. 3 (secondary), the pH of which was lowered to pH 1 and then elevated to pH 8.

Sample No. 4 (primary) referred to virus particles for the PEDV vaccine of Sample No. 2 coated with the pH-sensitive polymer. Sample No. 4 (secondary) referred to virus particles of Sample No. 4 (primary) additionally coated with a cationic polymer polylysine (pLys). And Sample No. 4 (low->high) indicated a result of Sample No. 4 (secondary), the pH of which was lowered to pH 1 and then elevated to pH 8.

Sample No. 5 (primary) referred to virus particles for the PEDV vaccine of Sample No. 2 coated with a pH-sensitive polymer. And Sample No. 5 (low->high) indicated a result of Sample No. 5 (primary), the pH of which was lowered to pH 1 and then elevated to pH 8.

As results, it can be confirmed that, when both the cationic polymer layer and the pH-sensitive polymer layer were formed, the virus particles (Sample No. 3 (low->high) and Sample No. 4 (low->high)) were stable even under a low pH condition, regardless of a coating layer stacking order. On the other hand, it can be confirmed that, when the coating layer was not formed or the pH-sensitive polymer was merely formed, stability was decreased.

As described above, the virus particles for oral virus vaccine according to the present disclosure can be effectively delivered to the intestines without being destroyed in the low pH environment of the gastrointestinal tract.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A polymer-coated porcine epidemic diarrhea virus particle for an oral vaccine, comprising:
   one or more porcine epidemic diarrhea virus particles for use as an oral vaccine;
   a cationic polymer layer; and a pH-sensitive polymer layer coating said one or more porcine epidemic diarrhea virus particles,
   wherein said cationic polymer layer and said pH-sensitive polymer layer are formed to coat said one or more porcine epidemic diarrhea virus particles, and any one of said cationic polymer layer and said pH-sensitive polymer layer is formed as an inner layer, and the other is formed as an outer layer, wherein:
   said cationic polymer layer comprises one or more cationic polymers selected from the group consisting of polylysine, polyhistidine, and polyarginine;
   said pH-sensitive polymer layer is ionized at pH 7 to 9; and
   said pH-sensitive polymer layer comprises one or more pH-sensitive polymers selected from the group consisting of poly(methacrylic acid-co-ethyl acrylate), poly (methacrylic acid-co-methyl methacrylate), and poly (methyl acrylate-co-methyl methacrylate-co-methacrylic acid).

2. The polymer-coated porcine epidemic diarrhea virus particle of claim 1, wherein said one or more porcine epidemic diarrhea virus particles have an average particle diameter of 0.1 μm to 10 μm.

3. The polymer-coated porcine epidemic diarrhea virus particle of claim 1, wherein said cationic polymer layer has an average thickness of 1 nm to 1 μm.

4. The polymer-coated porcine epidemic diarrhea virus particle of claim 1, wherein said pH-sensitive polymer layer has an average thickness of 1 nm to 1 μm.

5. A method of preparing the polymer-coated porcine epidemic diarrhea virus particle of claim 1, the method comprising:
   a step of formation of said inner layer to coat said one or more porcine epidemic diarrhea virus particles by mixing said one or more porcine epidemic diarrhea virus particles for use as an oral vaccine with one or more cationic polymers or one or more pH-sensitive polymers; and
   a step of formation of said outer layer to coat said inner layer by mixing said porcine epidemic diarrhea virus particles, which are coated by said inner layer, with said one or more cationic polymers or said one or more pH-sensitive polymers,
   wherein:
   any one of said one or more cationic polymers and said one or more pH-sensitive polymers forms said inner layer, and the other forms said outer layer
   said cationic polymer layer comprises one or more cationic polymers selected from the group consisting of polylysine, polyhistidine, and polyarginine;
   said pH-sensitive polymer layer is ionized at pH 7 to 9; and
   said pH-sensitive polymer layer comprises one or more pH-sensitive polymers selected from the group consisting of poly(methacrylic acid-co-ethyl acrylate), poly (methacrylic acid-co-methyl methacrylate), and poly (methyl acrylate-co-methyl methacrylate-co-methacrylic acid).

6. The method according to claim 5, wherein said formation of said pH-sensitive polymer layer is carried out at pH 7 or less.

7. An oral vaccine composition comprising the polymer-coated porcine epidemic diarrhea virus particle according to claim 1.

8. A feed composition comprising the polymer-coated porcine epidemic diarrhea virus particle according to claim 1.

9. A method of preventing infection with porcine epidemic diarrhea virus, the method comprising;
   orally administrating an effective amount of the polymer-coated porcine epidemic diarrhea virus particle according to claim 1 to a pig.

* * * * *